United States Patent
Rahtz et al.

[11] 3,968,219
[45] July 6, 1976

[54] HYDROXY PHENYLBUTAZONE DERIVATIVES AND THEIR PREPARATION

[75] Inventors: Dieter Rahtz; Henning Koch; Erich Gerhards, all of Berlin, Germany

[73] Assignee: Schering Aktiengesellschaft, Berlin & Bergkamen, Germany

[22] Filed: July 28, 1975

[21] Appl. No.: 599,397

[30] Foreign Application Priority Data
July 29, 1974 Germany.......................... 2436882

[52] U.S. Cl............................. 424/273; 260/310 B
[51] Int. Cl.².............. A61K 31/415; C07D 231/34; C07D 231/36
[58] Field of Search................ 260/310 B; 424/273

[56] References Cited
UNITED STATES PATENTS
3,457,273  7/1969  Rumpf et al. .................. 260/310 B FOREIGN PATENTS OR APPLICATIONS
7,009,718  1/1971  Netherlands .................. 260/310 B Primary Examiner—Donald B. Moyer
Attorney, Agent, or Firm—Millen, Raptes & White

[57] ABSTRACT

Bis-hydroxyphenylbutazone esters of alkanedioic acids of the formula

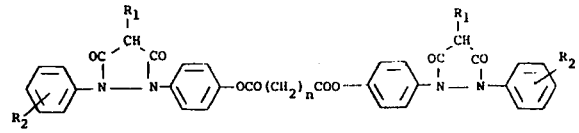

wherein $n$ is an integer from 1 to 18, inclusive; $R_1$ is hydrocarbon of 3–9 carbon atoms, optionally substituted by oxo or interrupted by thia, sulfinyl, or sulfonyl; and $R_2$ is a hydrogen atom, a fluorine atom, a chlorine atom, lower alkyl of 1–4 carbon atoms, or trifluoromethyl, preferably in the ortho or para position, possess topical anti-inflammatory activity.

14 Claims, No Drawings

HYDROXY PHENYLBUTAZONE DERIVATIVES AND THEIR PREPARATION

BACKGROUND OF THE INVENTION

This invention relates to novel hydroxyphenylbutazone derivatives having topical anti-inflammatory activity.

Phenylbutazones, e.g., 4-butyl-1-(4-hydroxyphenyl)2-phenyl-3,5dipyrazolidinedione, having systemic anti-inflammatory activity are known. This invention is directed to hydroxyphenylbutazone derivatives having topical anti-inflammatory activity.

SUMMARY OF THE INVENTION

In a composition aspect, this invention relates to novel hydroxyphenylbutazone derivatives of the general Formula I:

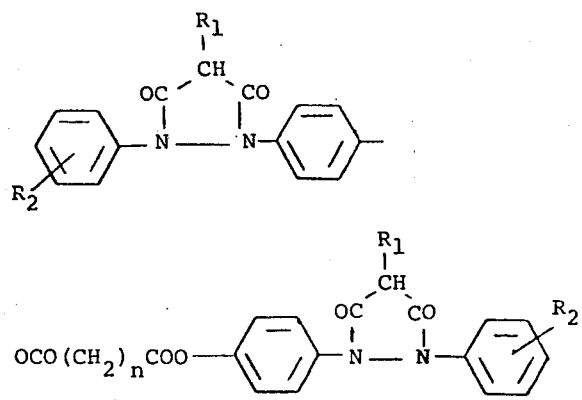

wherein $n$ is an integer from 1 to 18, inclusive; $R_1$ is hydrocarbon of 3–9 carbon atoms, optionally substituted by oxo or interrupted by thia, sulfinyl, or sulfonyl; and $R_2$ is a hydrogen atom, a fluorine atom, a chlorine atom, lower alkyl of 1–4 carbon atoms, or trifluoromethyl, preferably in the ortho or para position.

In another composition aspect, this invention relates to pharmaceutical compositions adapted for topical administration comprising one or more compounds of Formula I.

In process aspects, this invention relates to processes for the production and use of anti-inflammatory agents of the novel compounds of this invention.

DETAILED DISCUSSION

It is known that hydroxyphenylbutazone and its derivatives of general Formula II

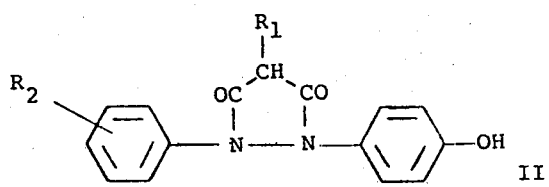

wherein $R_1$ and $R_2$ have the values given above are pharmacologically active compounds possessing, in particular, strong anti-inflammatory acitivity.

A pronounced anti-inflammatory activity has been observed particularly in those hydroxyphenylbutazone derivatives of general Formula II wherein $R_1$ is straight-chain or branched alkyl or cycloalkyl of 3–7 carbon atoms, such as, for example, butyl, isobutyl, pentyl, isopentyl, hexyl, cyclopentyl, and cyclohexyl, 3-oxobutyl, 3-methyl-2-butenyl, 2-phenylthioethyl, 2-phenylsulfinylethyl, and 2-phenylsulfonylethyl. These known hydroxyphenylbutazone derivatives are employed primarily for the systemic treatment of inflammatory conditions, such as, for example, inflammations of the joint. When applied topically, e.g., for the treatment of dermatoses of an inflammatory genesis, these conventional hydroxyphenylbutazone derivatives are of low effectiveness.

It has now been found that the alkanedioic bis-esters (Formula I) esters of these hydroxyphenylbutazone derivatives possess surprisingly high topical anti-inflammatory activity.

Examples of $R_1$ groups of Formula I, in addition to those values given above for Formula II are n-propyl, isopropyl, heptyl, n-octyl, n-nonyl, phenyl, p-tolyl, benzyl, phenethyl, 2-phenylpropyl and 3-phenylpropyl.

Examples of $R_2$ lower alkyl groups are methyl, ethyl n-propyl, isopropyl, n-butyl, isobutyl and tert.-butyl.

Preferred compounds of Formula I are those wherein:

a. $R_1$ is lower alkyl, more preferably n-butyl;
b. $R_2$ is a hydrogen atom or a substituent in the ortho or p-position, including those of (a);
c. $n$ is 1,3–7, inclusive, or 14, including those of (a) and (b).

Examples of compounds of this invention, in addition to those of the examples hereinafter are:

The malonic glutaric, adipic, pimetic, suberic, azelic and hexadecandioic acid bis esters of 4-cyclopentyl-1-(4-hydroxylphenyl)-2-phenyl-3,5pyrazolidinedione;

4-(3'-oxobutyl)-1-(4-hydroxyphenyl)-2-phenyl-3,5-pyrazolidinedione;

4-(3'-methyl-2'-butenyl)-1-(4-hydroxylphenyl)-2-phenyl-3,5-pyrazolidinedione;

4-(2'-phenylthioethyl)-1-(4-hydroxyphenyl)-2-phenyl-3,5-pyrazolidinedione;

4-(2'-phenylsulfinylethyl)-1-(4-hydroxylphenyl)-2-phenyl-3,5-pyrazolidinedione;

4-(2'-phenylsulfonylethyl)-1-(4-hydroxylphenyl)-2-phenyl-3,5-pyrazolidinedione;

4-butyl-1-(4-hydroxyphenyl)-2-(4'-fluorophenyl)-3,5-pyrazolidinedione;

4-butyl-1-(4-hydroxyphenyl)-2-(4'-chlorophenyl)-3,5-pyrazolidinedione;

4-butyl-1-(4-hydroxyphenyl)-2-(4'tolyl)-3,5-pyrazolidinedione; and 4-butyl-1-(4-hydroxyphenyl)-2-(3'-trifluoromethyl)-3,5-pyrazolidinedione.

In a process aspect, this invention relates to a process for the production of the novel hydroxyphenylbutazone derivatives of general Formula I, wherein a. a hydroxyphenylbutazone derivative of general Formula II is esterified with a dicarboxylic acid derivative of general Formula III $$XOC(CH_2)_nCOX$$

wherein n has the values given and each X is hydroxy, a chlorine atom, formyl, trifluoroacetyloxy, an alkoxycarbonyl or alkoxy, each alkoxy being of 1–4 carbon atoms; or b. a bis-hydrazo compound of the general Formula IV

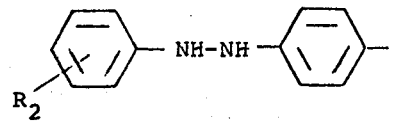

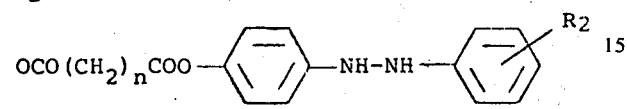

IV wherein n and $R_2$ have the values given above is condensed with a malonic acid derivative of general Formula V

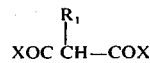

wherein X and $R_1$ have the values given above.

The process of this invention according to variant (a) can be conducted in a conventional manner. Thus, the hydroxyphenylbutazone derivatives of general Formula II can be reacted, for example, with a dicarboxylic acid chloride or the mixed anhydride of the dicarboxylic acid in the presence of an alkaline catalyst, e.g., triethylamine, N-ethyl-morpholine, pyridine, lutidine, collidine, 4-dimethylaminopyridine, sodium carbonate, sodium bicarbonate, potassium carbonate, potassium bicarbonate, sodium hydroxide or potassium hydroxide, under the usual conditions.

It is also possible to react the hydroxyphenylbutazone derivatives of general Formula II with a dicarboxylic acid ester of general Formula III in the presence of an acidic catalyst, e.g., hydrogen chloride, sulfuric acid, p-toluenesulfonic acid, trifluoroacetic acid or boron trifluoride.

The aforementioned methods, however, have the disadvantage that normally also the enolized oxo groups of the hydroxyphenylbutazone derivatives are partially esterified at the same time. To avoid this, the esterification is suitable conducted by reacting the hydroxyphenylbutazone derivatives of general Formula II with a dicarboxylic acid of general Formula III in the presence of a dehydrating agent, such as, for example, carbonyl diimidazole, dicyclohexylcarbodiimide, or polyphosphoric acid esters.

The esterification according to process variant (a) is preferably effected using, per mole of dicarboxylic acid derivative of general Formula III, 2 to 5 moles of a hydroxy-phenylbutazone derivative of general Formual II, the reaction conditions being chosen so that the hydroxyphenylbutazone derivative of general Formula II is present in excess in the reaction mixture.

The process of this invention according to variant (b) is conducted under the conditions customarily employed for the production of phenylbutazone derivatives from hydrazo compounds. Thus, for example, the bis-hydrazo compounds of general Formula IV can be reacted with a malonic acid dichloride or a mixed anhydride of the substituted malonic acid in the presence of an alkaline catalyst, e.g., pyridine, collidine, lutidine, 4dimethylaminopyridine sodium or potassium carbonate, or sodium or potassium hydroxide, under the usual conditions.

The bis-hydrazo compounds of general Formula IV required as the starting materials can be prepared, in a simple manner and under the conditions described in process variant (a), from the dicarboxylic acid derivatives of general Formula III and the hydrazo compounds of general Formula VI

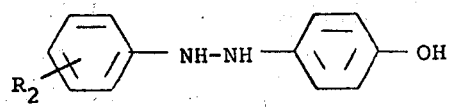

wherein $R_2$ has the values given above.

The novel hydroxyphenylbutazone derivtives of general Formula I are pharmacologically active. In particular, they exhibit strong anti-inflammatory activity upon topical application in the treatment of dermatoses of an inflammatory origin. They differ in this respect from already known hydroxyphenylbutazone derivatives, which have a substantially weaker effect when applied topically.

The topical anti-inflammatory activity of the novel hydroxyphenylbutazone derivatives can be determined employing the conventional vasoconstriction test as follows:

On the backs of volunteers for the experiment, the stratum corneum was abraded by the application and tearing off of adhesive tape, conducted 20 times at the same spot, thus producing a pronounced hyperemia. Within the stripped area, respectively 50 mg of ointment containing in each case 0.1% and 0.01%, respectively, of the substance to be tested or of the reference substance in a water-oil base was applied on marked areas. The extent of the vasoconstriction was determined one, four, and eight hours after application.

In order to evaluate the vasoconstriction, which is a representative syndrome of topical anti-inflammatory activity the color values of the untreated stripped skin and the treated stripped skin were determined and compred with the color value of the normal skin, wherein the color value of the normal skin was set to be equal to 100 and the color value of the untreated stripped skin was fixed at 0. Minor, moderate, and high-grade vasoconstriction was evaluated with values between 0 and 100. The results are shown in Table I below in which two compounds of this invention (III, IV) were compated with hydroxyphenylbutazone (I) and fluorocortolone. As can be seen, the novel compounds are substantially more active than hydroxyphenylbutazone.

TABLE I

| | Vasoconstriction Test | | | |
|---|---|---|---|---|
| | | | Observation Time in Hours | |
| No. | Compound | Active Agent Conc. | 1   4 | 8 |
| I | 4-Butyl-1-(4-hydroxyphenyl)-2-phenyl-3,5-pyrazolidinedione [= Hydroxyphenylbutazone] | 0.1 | 15   35 | 33 |
| | | 0.01 | 18   25 | 24 |
| II | 6α-Fluoro-11β,21-dihydroxy-16γ-methyl-1,4-pregnadiene-3,20- | 0.1 | 35   75 | 85 |

TABLE I-continued

| | | Vasoconstriction Test | | | |
|---|---|---|---|---|---|
| | | | Observation Time in Hours | | |
| No. | Compound | Active Agent Conc. | 1 | 4 | 8 |
| | dione [= Fluocortolone] | 0.01 | 15 | 65 | 85 |
| III | Adipic Acid Bis[4-(4-butyl-3,5-dioxo-2-phenylpyrazolidinyl)-phenyl Ester] | 0.1 | 44 | 72 | 78 |
| | | 0.01 | 34 | 66 | 70 |
| IV | Pimelic Acid Bis[4-(4-butyl-3,5-dioxo-2-phenylpyrazolidinyl)-phenyl Ester] | 0.1 | — | 65 | 67 |
| | | 0.01 | — | 44 | 49 |

The anti-inflammatory activity of the novel hydroxyphenylbutazone derivatives upon topical application can also be determined in accordance with the Tonelli method, as follows:

The compound to be tested is dissolved in an irritant consisting of 4 parts of pyridine, 1 part of distilled water, 5 parts of ether, and 10 parts of a 4% ether croton oil solution. Felt strips attached to the insides of a slide tweezers are saturated with this text solution and pressed under slight pressure for 15 seconds onto the right ear of male rats weighing 100–160 g.

The left ear remains untreated and serves as control. Three hours after application, the animals are sacrificed and disks of a size of 9 mm. are punched out of their ears. The weight difference between the disk from the right ear and that of the left ear is a measure for the thus-formed edema.

Control animals are treated in the same way, except that the irritant solution employed does not contain any test compound.

The concentrations of effective agent ($ED_{50}$) are determined which, when employed, cause a 50% reduction in the formation of edema.

TABLE II

| No. | Compound | Edema Test $ED_{50}$ (mg./ml.) |
|---|---|---|
| I | 4-Butyl-1-(4-hydroxyphenyl)-2-phenyl-3,5-pyrazolidinedione [= Hydroxyphenylbutazone] | 8 |
| II | 6α-Fluoro-11β,21-dihydroxy-16α-methyl-1,4-pregnadiene-3,20-dione [= Fluocortolone] | 3.4 |
| III | Adipic Acid Bis[4-(4-butyl-3,5-dioxo-2-phenylpyrazolidinyl)-phenyl Ester] | 2.1 |
| IV | Pimelic Acid Bis[4-(4-butyl-3,5-dioxo-2-phenylpyrazolidinyl)-phenyl Ester] | 4.2 |

It can be seen from the tables that the novel hydroxyphenylbutazone derivatives are distinguished over the known compounds of analogous structure by a superior anti-inflammatory activity. The anti-inflammatory effectiveness of the novel hydroxyphenylbutazone derivatives is, upon local administration, approximately as strong as that of conventional corticoids showing anti-inflammatory activity.

Consequently, the present invention provides non-steroidal compounds which, when topically administered, possess an excellent anti-inflammatory activity.

The corticoids heretofore utilized for the treatment of skin inflammations usually possess, in addition to the topical effect, also a systemic effect. Even when applied topically, these corticoids can enter the bloodstream due to resorption through the inflamed skin or due to skin injuries, where they affect the body functions in a variety of ways as hormone-active substances.

This disadvantage does not exist in the the topically effective hydroxyphenylbutazone derivatives of the present invention. Moreover, the hydroxyphenylbutazone derivatives have the advantage of low toxicity.

The novel compounds are suitable, in combination with the vehicles customary in galenic pharmacy for the local treatment of allergies, contact dermatitis, eczemas of a great variety of types, neurodermatitis, erythrodermia, burns, pruritus vulvae et ani, rosacea, erythematodes cutaneus, psoriasis, lichen ruber planus et verrucosus, and similar skin diseases.

The special medicinal preparations are produced in the usual way by converting the active agents with suitable additives into the desired form of application, such as, for example: solutions, lotions, ointments, creams, inhalants, or plasters. In the thus-formulated forms of application, the concentration of effective agent is dependent on the manner in which it is administered. In case of lotions and ointments, an effective agent concentration of 0.005% to 5% is preferably utilized.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

Two grams of 4-butyl-1-(4-hydroxyphenyl)-2-phenyl-3,5-pyrazolidinedione is dissolved in 50 ml. of anhydrous chloroform, and 6.7 g. of the ethyl ester of polyphosphoric acid (preparation: Y. Kanaoka et al., Chemistry and Industry 1964, 2102) and 0.565 g. of azelaic acid are added thereto. While the polyphosphoric acid ester is immediately dissolved, the azelaic acid remains undissolved at first. The reaction mixture is refluxed under nitrogen for 2 hours, thus dissolving the azelaic acid and forming an oil, which separates. The solution is decanted off from the oil and freed to a maximum extent from the chloroform under vacuum. The residue of the evaporation crystallizes upon the addition of ice and water. The crystals are washed thoroughly with water, dried, and recrystallized twice from Methanol, yielding 1.5 g. of azelaic acid bis[4-(4-butyl-3,5-dioxo-2-phenylpyrazolidinyl)-phenylester], m.p. 77°–79° C.

Analogously, 4-butyl-1-(4-hydroxyphenyl)-2-phenyl-3,5-pyrazolidinedione is reacted with malonic acid, adipic acid, pimelic acid, suberic acid, and hexadecanedioic acid, thus obtaining the following compounds:

malonic acid bis[4-(4-butyl-3,5-dioxo-2-phenylpyrazolidinyl)phenyl ester]
adipic acid bis[4-(4-butyl-3,5-dioxo-2-phenylpyrazolidinyl)-phenyl ester], m.p. 128°–131° C.
pimelic acid bis[4-(4-butyl-3,5-dioxo-2-phenylpyrazolidinyl)-phenyl ester], m.p. 122°–125° C.
suberic acid bis[4-(4-butyl-3,5-dioxo-2-phenylpyrazolidinyl)-phenyl ester], m.p. 78°–80° C.
hexadecanedioic acid bis[4-(4-butyl-3,5-dioxo-2-phenylpyrazolidinyl)-phenyl ester] (not obtained in crystalline form).

EXAMPLE 2

At 0°–5° C., a solution of 2.5 g. of adipic acid bis(4-phenylhydrazophenyl)ester in 200 ml. of chloroform is added dropwise to a solution of 1.9 g. of butylmalonic acid dichloride and 1.7 ml. of pyridine in 20 ml. of chloroform. The reaction mixture is allowed to stand overnight at room temperature. Thereafter, the mixture is washed first with 0.1N hydrochloric acid and then with water, and concentrated by evaporation. The residue is recrystallized from Methanol. The yield is 2 g. of adipic acid bis[4-(4-butyl-3,5-dioxo-2-phenylpyrazolidinly)-phenyl ester], m.p. 128°–131° C.

The adipic acid bis(4-phenylhydrazophenyl)ester required for the synthesis is prepared as follows:

A. 164 g. of polyphosphoric acid ethyl ester is dissolved in 60 ml. of chloroform. A suspension of 14.86 g. of adipic acid and 40.0 g. of p-(phenylazo)-phenol in 340 ml. of chloroform is added to this solution. The reaction mixture is agitated for 4 hours. Then, 35 g. of adipic acid bis(4-phenylazophenyl)ester is obtained by vacuum-filtering the reaction mixture; this product is recrystallized from ethyl acetate. In this way, 30 g. of a pure compound is obtained, m.p. 176°–177° C.

B. 5 g. of adipic acid bis(4-phenylazophenyl)ester is hydrogenated in a shake flask in an ethyl acetate - pyridine mixture with 10% palladium charcoal as the catalyst, at room temperature and under normal pressure. After the stoichiometric amount of hydrogen has been absorbed, the catalyst is filtered off, the colorless solution is evaporated under nitrogen, and the residue is recrystallized from methanol. Yield: 3 g. of adipic acid bis(4-phenylhydrazophenyl)ester, m.p. 167°–171° C.

EXAMPLE 3

6.5 g. of 4-butyl-1-(4-hydroxyphenyl)-2-phenyl-3,5-pyrazolidinedione is dissolved in a mixture of 50 ml. of anhydrous chloroform and 12 ml. of pyridine. Under agitation and in a nitrogen atmosphere, 1.9 g. of pimelic acid dichloride is added dropwise at 0°–5° C. to this solution. The reaction mixture is allowed to stand overnight with the exclusion of moisture and under room temperature. The mixture is then evaporated and the residue decomposed with ice and a small amount of hydrochloric acid. The reaction product is separated, dried, and recrystallized from Methanol. The yield is 2 g. of pimelic acid bis[4-(4-butyl-3,5-dioxo-2-phenylpyrazolidinyl)-phenyl ester], m.p. 122°–125° C.

EXAMPLE 4

10 g. of 4-butyl-1-(4-hydroxyphenyl)-2-phenyl-3,5-pyrazolidinedione is dissolved in 500 ml. of anhydrous carbon tetrachloride. To this mixture are added 2.04 g. of glutaric acid and 33.3 g. of the ethyl ester of polyphosphoric acid. The phosphoric acid ester is only partially dissolved; the glutaric acid remains practically undissolved. The reaction mixture is refluxed for 2 hours under nitrogen, thus dissolving the glutaric acid. After cooling, the mixture is decanted off from an undissolved oil. The solution is concentrated by evaporation under vacuum. The residue of this evaporation is mixed with ice water. The resultant milky oil is recrystallized from isopropanol. After recrystallization from this solvent, 1 g. of glutaric acid bis[4-(4-butyl-3,5-dioxo-2-phenylpyrazolidinyl)-phenyl ester] is obtained in the form of colorless crystals having a melting point of 147°–150° C.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A hydroxyphenylbutazone derivative of the formula:

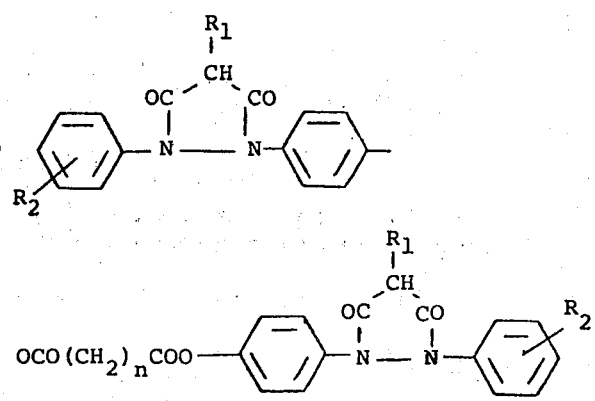

wherein $n$ is an integer from 1 to 18, inclusive; $R_1$ is hydrocarbon of 3–9 carbon atoms, unsubstituted or substituted by oxo or interrupted by a thia, sulfinyl, or sulfonyl group, and $R_2$ is a hydrogen atom, a fluorine atom, a chlorine atom, alkyl of 1 to 4 carbon atoms, or trifluoromethyl.

2. A compound of claim 1, wherein $R_2$ is a hydrogen atom.

3. A compound of claim 1, wherein $n$ is 1,3–7, inclusive, or 14.

4. A compound of claim 1, wherein $R_1$ is butyl.

5. A compound of claim 4, wherein $R_2$ is a hydrogen atom.

6. Azelaic acid bis [4-(4-butyl-3,5-dioxo-2-phenylpyrazolidinyl)-phenyl ester], a compound of claim 1.

7. Malonic acid bis [4-(4-butyl-3,5-dioxo-2-phenylpyrazolidinyl)-phenyl ester], a compound of claim 1.

8. Adipic acid bis [4-(4-butyl-3,5-dioxo-2-phenylpyrazolidinyl)-phenyl ester], a compound of claim 1.

9. Pimelic acid bis [4-(4-butyl-3,5-dioxo-2-phenylpyrazolidinyl)-phenyl ester], a compound of claim 1.

10. Suberic acid bis [4-(4-butyl-3,5-dioxo-2-phenylpyrazolidinyl)-phenyl ester], a compound of claim 1.

11. Hexadecanedioic acid bis [4-(4-butyl-3,5-dioxo-2-phenylpyrazolidinyl)-phenyl ester], a compound of claim 1.

12. Glutaric acid bis [4-(4-butyl-3,5-dioxo-2-phenylpyrazolidinyl)-phenyl ester], a compound of claim 1.

13. A pharmaceutical composition comprising in unit dosage form an anti-inflammatory effective amount of at least one compound of claim 1 in admixture with a pharmaceutically acceptable carrier adapted for topical administration.

14. A method of treating inflammatory conditions of the skin which comprises administering topically to the affected skin an anti-inflammatorily effective amount of a compound of claim 1.

* * * * *